(12) United States Patent
Woerden et al.

(10) Patent No.: US 11,167,144 B2
(45) Date of Patent: Nov. 9, 2021

(54) APPARATUS FOR TERMINATING OR UNPINNING ROTATING ELECTRIC ACTIVITY IN A CARDIAC TISSUE

(71) Applicant: Max-Planck-Gesellschaft zur Foerderung der Wissenschaften e.V., Munich (DE)

(72) Inventors: Henrik tom Woerden, Goettingen (DE); Daniel Hornung, Goettingen (DE); Tariq Baig-Meininghaus, Eberhausen (DE)

(73) Assignee: MAX-PLANCK-GESELLSCHAFT ZUR FOERDERUNG DER WISSENSCHAFTEN E.V., Munich (DE)

( * ) Notice: Subject to any disclaimer, the term of this patent is extended or adjusted under 35 U.S.C. 154(b) by 329 days.

(21) Appl. No.: 16/447,218

(22) Filed: Jun. 20, 2019

(65) Prior Publication Data

US 2019/0298999 A1  Oct. 3, 2019

Related U.S. Application Data

(63) Continuation of application No. PCT/EP2017/082048, filed on Dec. 8, 2017.

(30) Foreign Application Priority Data

Jan. 3, 2017  (EP) ..................................... 17150209

(51) Int. Cl.
*A61N 1/36* (2006.01)
*A61N 1/362* (2006.01)
(Continued)

(52) U.S. Cl.
CPC ........... *A61N 1/3621* (2013.01); *A61N 1/365* (2013.01); *A61N 1/3906* (2013.01); *A61N 1/3624* (2013.01)

(58) Field of Classification Search
CPC .... A61N 1/3621; A61N 1/3906; A61N 1/365; A61N 1/3624
See application file for complete search history.

(56) References Cited

U.S. PATENT DOCUMENTS

| 8,014,858 | B1 | 9/2011 | Ben-Haim et al. |
| 8,473,051 | B1 | 6/2013 | Wessels et al. |
| (Continued) | | | |

FOREIGN PATENT DOCUMENTS

| WO | 0072918 A1 | 12/2000 |
| WO | 2011139596 A2 | 11/2011 |
| WO | 2012172027 A2 | 12/2012 |

OTHER PUBLICATIONS

PCT International Search Report and Written Opinion in related, co-pending PCT Application No. PCT/EP2017/082048, dated Apr. 4, 2018.

*Primary Examiner* — Rex R Holmes
(74) *Attorney, Agent, or Firm* — Thomas | Horstemeyer, LLP

(57) ABSTRACT

An apparatus for terminating or unpinning rotating electric activity in a cardiac tissue analyzes an electric parameter for rotating electric activity in the cardiac tissue, and generates electric pulses in response to the rotating electric activity. The electric pulses are applied as electric field pulses and include a plurality of rotating electric activity synchronization pulses arranged at first intervals and a rotating electric activity termination or unpinning pulse following to the last synchronization pulse at a second interval which is similar to one of the first intervals. A maximum electric field strength caused the synchronization pulses is not more than 82% of a maximum electric field strength caused by the termination or unpinning pulse, and an electric pulse energy delivered to the cardiac tissue by each of the synchronization (Continued)

pulses is not more than 67% of an electric pulse energy delivered by the termination or unpinning pulse.

20 Claims, 5 Drawing Sheets

(51) Int. Cl.
    *A61N 1/365*     (2006.01)
    *A61N 1/39*     (2006.01)

(56) References Cited

U.S. PATENT DOCUMENTS

| | | |
|---|---|---|
| 8,509,889 B2 | 8/2013 | Efimov et al. |
| 8,560,066 B2 | 10/2013 | Efimov et al. |
| 8,706,216 B2 | 4/2014 | Efimov et al. |
| 8,874,208 B2 | 10/2014 | Efimov et al. |
| 8,886,309 B2 | 11/2014 | Luther et al. |
| 9,233,248 B2 | 1/2016 | Luther et al. |
| 9,289,620 B2 | 3/2016 | Efimov et al. |
| 9,526,907 B2 | 12/2016 | Efimov et al. |
| 9,814,895 B2 | 11/2017 | Efimov et al. |
| 10,099,062 B2 | 10/2018 | Efimov et al. |
| 2004/0172065 A1 | 9/2004 | Sih et al. |
| 2006/0095082 A1 | 5/2006 | Sih et al. |
| 2006/0100670 A1 | 5/2006 | Sweeney |
| 2008/0306561 A1 | 12/2008 | Sweeney |

APPARATUS FOR TERMINATING OR UNPINNING ROTATING ELECTRIC ACTIVITY IN A CARDIAC TISSUE

CROSS REFERENCE TO RELATED APPLICATIONS

This application is a continuation to International Application PCT/EP2017/082048 with an international filing date of Dec. 8, 2017 entitled "Apparatus for Terminating or Unpinning Rotating Electric Activity in a Cardiac Tissue" and claiming priority to co-pending European Patent Application No. EP 17 150 209.9 also entitled "Apparatus for Terminating or Unpinning Rotating Electric Activity in a Cardiac Tissue" and filed on Jan. 3, 2017.

FIELD OF THE INVENTION

The present invention relates to an apparatus for terminating or unpinning rotating electric activity in a cardiac tissue. The rotating electric activity may, for example, be associated with an electric state of the cardiac tissue called fibrillation. The electric activity may include so-called scroll waves. The rotating electric activity may rotate about inhomogeneities of the cardiac tissue. The cardiac tissue may be a living heart.

BACKGROUND

WO 2012/172027 A2 discloses an apparatus for terminating a high frequency arrhythmic electric state of a biological tissue. The known apparatus comprises a termination unit which determines from an electric signal representative of the present electric state of the biological tissue at least one dominant frequency. From the at least one dominant frequency the termination unit determines whether the present electric state of the biological tissue is a high frequency arrhythmic electric state. Further the determination unit determines from the electric signal a dominance level indicative of how dominant the at least one dominant frequency is in the high frequency arrhythmic electric state. At a point in time at which the dominance level exceeds a predefined threshold value, the determination unit triggers an electric pulse generator to generate at least one series of electric pulses at intervals depending on the at least one dominant frequency. These electric pulses are applied to the biological tissue via at least one electrode connected to the pulse generator. For determining the dominance level, the determination unit compares the intensity of the electric signal of the dominant frequency with the intensity of the electric signal at at least one neighboring frequency. The electric pulse generator generates electric pulses at a comparatively low electric energy as compared to a standard defibrillation energy used for defibrillation by means of a single pulse providing an electric shock. The electric pulse generator generates the individual electric pulses of the at least one series of electric pulses at such time intervals that the electric pulses raster scan the phase defined by the at least one dominant frequency at phase intervals. For this purpose, the electric pulse generator generates the electric pulses of the at least one series of electric pulses at time intervals deviating from the reciprocal value of the at least one dominant frequency by $\frac{1}{32}$ to $\frac{1}{5}$ of the reciprocal value of the at least one dominant frequency. Preferably, the intervals of the electric pulses exceed the reciprocal value of the dominant frequency. If the determination unit determines from the electrical signal that the biological tissue still is in the arrhythmic electric state after a first series of electric pulses has been applied, the electric pulse generator generates a further series of electric pulses at a higher voltage than the first series of electric pulses. Only if the termination unit, after a predefined number of series of electric pulses, determines that the biological tissues still is in the arrhythmic electric state, the electric pulse generator generates a single electric pulse of a standard heart defibrillation energy.

WO 2011/139596 A2 discloses a three-stage atrial cardioversion therapy. A first stage of the three-stage atrial cardioversion therapy has at least two and less than ten biphasic atrial cardioversion pulses of more than 10 V and less than 100 V with a pulse duration of less than 10 milliseconds and a pulse coupling interval of between 20 to 50 ms, wherein the first stage has a total duration of less than two of the cycle lengths of a detected atrial arrhythmia and is delivered within a ventricular refractory period with an energy of each biphasic atrial cardioversion pulse being less than 0.1 J to unpin one or more singularities associated with the atrial arrhythmia. A second stage of the three-stage atrial cardioversion therapy has at least five and less than ten far field pulses of less than a ventricular far-field excitation threshold with a pulse duration of more than 5 and less than 20 ms and a pulse coupling interval of between 70 to 90% of the cycle length of the atrial arrhythmia, wherein the second stage prevents repining of the one or more singularities associated with the atrial arrhythmia that are unpinned by the first stage. The third stage of the three-stage cardioversion therapy has at least five and less than ten near field pulses of less than 10 V with a pulse duration of more than 0.2 and less than 5 ms and a pulse coupling interval of between 70 to 90% of the cycle length of the atrial arrhythmia, wherein the third stage extinguishes the one or more singularities associated with the atrial arrhythmia that are unpinned by the first stage and prevented from repining by the second stage.

U.S. Pat. No. 8,014,858 B1 discloses a method of terminating a fibrillation occurring in a heart of a person without applying shock pulses by applying electrical pulses to the heart at a rate greater than about 10 Hz, with a peak power that is less than about 100 W, wherein applying the pulses comprises applying a pulse having an amplitude less than about 50 mA, and terminating the electric pulses, whereby the steps of applying and terminating the electric pulses effectuate defibrillation of the heart. In the known method motion of the heart is sensed, and applying the pulses comprises modifying a characteristic of at least some of the pulses applied to the heart responsive to the sensed motion, and pacing the heart at approximately 1 Hz while applying the electrical pulses at the rate greater than about 10 Hz.

U.S. Pat. No. 8,473,051 B1 discloses a method of treating atrial arrhythmias by delivering a multi-stage atrial cardioversion therapy. Each stage of the multi-stage atrial cardioversion therapy includes at least two and less than ten atrial cardioversion pulses of more than 10 volts and less than 500 V for the pulse duration of less than 10 ms, each pulse comprising multiple sub-pulses having a sub-pulse duration of less than 10 ms of increasing, decreasing or constant amplitudes.

There is still a need of an apparatus for terminating or unpinning rotating electric activity in a cardiac tissue which applies electric pulses to the cardiac tissue at a lower overall electric energy than known apparatuses but nevertheless effectively terminates or unpins the rotating electric activity.

SUMMARY OF THE INVENTION

The present invention relates to an apparatus for terminating or unpinning rotating electric activity in a cardiac tissue. The apparatus comprises an electric state sensor configured to sense at least one electric parameter of the cardiac tissue; an electric state analyzer connected to the electric state sensor and configured to analyze the at least one electric parameter sensed by the electric state sensor for rotating electric activity in the cardiac tissue; a pulse generator connected to the electric state analyzer and configured to generate electric pulses in response to the electric state analyzer analyzing that there is rotating electric activity in the cardiac tissue, the electric pulses including a rotating electric activity termination or unpinning pulse; and a pulse applicator connected to the pulse generator and configured to apply the electric pulses as electric field pulses extending across the cardiac tissue. The electric pulses include a plurality of rotating electric activity synchronization pulses preceding the rotating electric activity termination or unpinning pulse. The rotating electric activity synchronization pulses are arranged at first intervals, and the rotating electric activity termination or unpinning pulse is arranged at a second interval in a range from 0.7 to 1.2 times one of the first intervals after the last one of the plurality of rotating electric activity synchronization pulses. A first maximum electric field strength as caused by each of the rotating electric activity synchronization pulses is not more than 82% of a second maximum electric field strength as caused by the rotating electric activity termination or unpinning pulse; and alternatively or additionally a first electric pulse energy delivered to the cardiac tissue by each of the rotating electric activity synchronization pulses is not more than 67% of a second electric pulse energy delivered to the cardiac tissue by the rotating electric activity termination or unpinning pulse.

The present invention further relates to an apparatus for terminating or unpinning rotating electric activity in a cardiac tissue. The apparatus comprises an electric state sensor configured to sense at least one electric parameter of the cardiac tissue; an electric state analyzer connected to the electric state sensor and configured to analyze the at least one electric parameter sensed by the electric state sensor for rotating electric activity in the cardiac tissue; a pulse generator connected to the electric state analyzer and configured to generate electric pulses in response to the electric state analyzer analyzing that there is rotating electric activity in the cardiac tissue, the electric pulses including a rotating electric activity termination or unpinning pulse; and a pulse applicator connected to the pulse generator and configured to apply the electric pulses as electric field pulses extending across the cardiac tissue. The electric pulses include a plurality of rotating electric activity synchronization pulses preceding the rotating electric activity termination or unpinning pulse. The rotating electric activity synchronization pulses are arranged at first intervals, and the rotating electric activity termination or unpinning pulse is arranged at a second interval in a range from 0.7 to 1.2 times one of the first intervals after the last one of the plurality of rotating electric activity synchronization pulses. A first maximum electric field strength as caused by each of the rotating electric activity synchronization pulses is not more than 71% of a second maximum electric field strength as caused by the rotating electric activity termination or unpinning pulse. A first electric pulse energy delivered to the cardiac tissue by each of the rotating electric activity synchronization pulses is not more than 50% of a second electric pulse energy delivered to the cardiac tissue by the rotating electric activity termination or unpinning pulse. A number of the rotating electric activity synchronization pulses preceding the rotating electric activity termination or unpinning pulse is in a range from 10 to 30. The first maximum electric field strength as caused by each of the rotating electric activity synchronization pulses is in a range from 20 to 200 V/m. The electric state analyzer is configured to analyze the at least one electric parameter sensed by the electric state sensor for a characteristic frequency of the rotating electric activity in the cardiac tissue, and that the pulse generator is configured to generate the rotating electric activity synchronization pulses at intervals at intervals longer than 0.6 times and shorter than 0.9 times a reciprocal value of the characteristic frequency of the rotating electric activity in the cardiac tissue; and the pulse applicator is configured to apply the rotating electric activity synchronization pulses and the rotating electric activity termination or unpinning pulse as electric field pulses extending between a same electrode and a same counter electrode.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
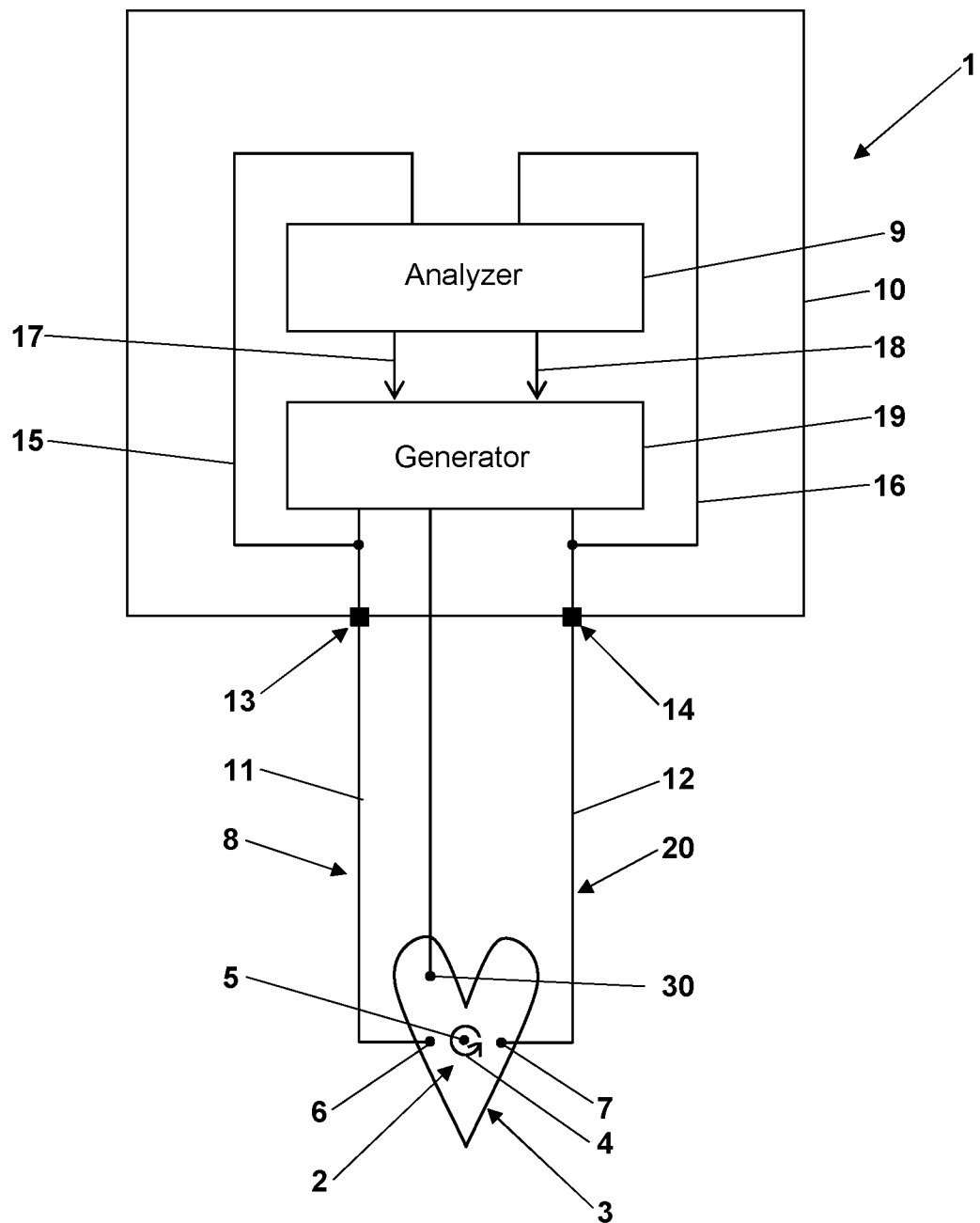
FIG. 1 is a schematic drawing of an apparatus for terminating or unpinning rotating electric activity in a cardiac tissue.

The apparatus for terminating or unpinning rotating electric activity in a cardiac tissue comprises an electric state sensor configured to sense at least one electric parameter of the cardiac tissue; an electric state analyzer connected to the electric state sensor and configured to analyze the at least one electric parameter sensed by the electric state sensor for rotating electric activity in the cardiac tissue; a pulse generator connected to the electric state analyzer and configured to generate electric pulses in response to the electric state analyzer analyzing that there is rotating electric activity in the cardiac tissue; and a pulse applicator connected to the pulse generator and configured to apply the electric pulses as electric field pulses extending across the cardiac tissue. The electric pulses include a rotating electric activity termination or unpinning pulse and a plurality of rotating electric activity synchronization pulses preceding the rotating electric activity termination or unpinning pulse. The rotating electric activity synchronization pulses are arranged at first intervals, and the electric activity termination or unpinning pulse is arranged at a second interval in a range from 0.7 to 1.2 of each of the first intervals after the last of the plurality of rotating electric activity synchronization pulses. At least one of a first maximum electric field strength as caused by each of the rotating electric activity synchronization pulses and a first electric pulse energy delivered to the cardiac tissue by each of the rotating electric activity synchronization pulses is not more than 82% of a second maximum electric field strength as caused by the rotating electric activity termination or unpinning pulse or not more than 67% of a second electric pulse energy delivered to the cardiac tissue by the rotating electric activity termination or unpinning pulse, respectively.

The apparatus for terminating or unpinning rotating electric activity in a cardiac tissue does not split up a single rotating electric activities unpinning or synchronization pulse into a plurality of rotating electric activity termination or unpinning pulses delivered at intervals to unpin or terminate rotating electric activity of different phases according to WO 2012/172027 A2. Instead, the rotating electric activity in the cardiac tissue is first synchronized with a plurality of rotating electric activity synchronization pulses and then terminated or unpinned by a single rotating electric activity termination or unpinning pulse or by two rotating electric activity termination or unpinning pulses. A second rotating electric activity termination or unpinning pulse already considerably increases the total energy applied to the cardiac tissue for terminating or unpinning the rotating electric activity. For this reason, groups of three or more separate rotating electric activity termination or unpinning pulses are not according to the present disclosure. The rotating electric activity synchronization pulses do not qualify as fully suitable rotating electric activity termination or unpinning pulses due to their lower maximum electric field strength and/or lower electric pulse energy. This does, however, not exclude that the rotating electric activity synchronization pulses do already terminate or unpin any weak rotating electric activity. With stronger rotating electric activity, however, the rotating electric activity synchronization pulses may, however, not be strong enough to terminate or unpin them. With regard to these stronger rotating electric activity, the rotating electric activity synchronization pulses will, however, be able to cause some kind of a synchronization such that they are prone to easy termination or unpinning by means of the following rotating electric activity termination or unpinning pulse. In other words, due to the application of the rotating electric activity synchronization pulses, it is not necessary to scan the phase with a plurality of rotating electric activity termination or unpinning pulses. Instead, a succeeding single rotating electric activity termination or unpinning pulse will be sufficient.

The total energy applied to the cardiac tissue for terminating or unpinning the rotating electric activity can thus be strongly reduced as compared to a plurality of rotating electric activity termination or unpinning pulses of equal electric field strength and electric pulse energy according to WO 2012/172027 A2, as the rotating electric activity synchronization pulses are of a considerably reduced maximum electric field strength and/or electric pulse energy.

Particularly, the first electric pulse energy delivered to the cardiac tissue by each of the rotating electric activity synchronization pulses being not more than 67% of the second electric pulse energy delivered to the cardiac tissue by the rotating electric activity termination or unpinning pulse means that a ratio between the first and the second electric pulse energy is not more than about 2:3. Due to the fact that the electric energy depends on the square of the electric field strength, the first maximum electric field strength as caused by each of the rotating electric activity synchronization pulses being not more than 82% of the second maximum electric field strength as caused by the rotating electric activity termination or unpinning pulse means about the same as the criterion on the first and second electric pulse energies with same shapes of the rotating electric activity synchronization and termination or unpinning pulses (82%× 82%=67%).

The final rotating electric activity termination or unpinning pulse delivered by the apparatus for terminating or unpinning rotating electric activity in a cardiac tissue may be of a same second maximum electric field strength and/or second electric pulse energy as known as each pulse of a plurality of same rotating electric activity termination or unpinning pulses according to WO 2012/172027 A2.

In the apparatus for terminating or unpinning rotating electric activity in a cardiac tissue a same pair of electrodes may both be part of the electric state analyzer and the pulse applicator.

Typically, a number of the rotating electric activity synchronization pulses preceding the rotating electric activity termination or unpinning pulse is at least 5. Often, this number is in a range from 10 to 30. Sometimes this number is about 15 to 25.

Often, it will be sufficient that the first maximum electric field strength as caused by each of the rotating electric activity synchronization pulses is not more than 71% or not more than 50% of the second maximum electric field strength as caused by the rotating electric activity termination or unpinning pulse. In absolute terms, the first maximum electric field strength as caused by all of the rotating electric activity synchronization pulses may be in a range from 20 to 300 V/m. Typically it is not more than 200 V/m. The first electric field strength caused by each of the rotating electric activity synchronization pulses may further be constant, i.e. the same with all of the rotating electric activity synchronization pulses.

The first electric pulse energy delivered to the cardiac tissue by each of the rotating electric activity synchronization pulses may be not more than 50% or even not more than 25% of the second electric pulse energy delivered to the cardiac tissue by the rotating electric activity termination or unpinning pulse. In absolute terms, the first electric pulse energy delivered to the cardiac tissue by each of the rotating electric activity synchronization pulses may be in a range from 0.005 to 20 J. This rather large range is due to the fact that the geometries under which electrodes for applying the pulses are arranged may vary strongly. Further, the first electric pulse energy delivered to the cardiac tissue by each of the rotating electric activity synchronization pulses may be constant, i.e. the same with all of the rotating electric activity synchronization pulses.

In the apparatus for terminating or unpinning rotating electric activity in a cardiac tissue, the electric state analyzer may be configured to analyze the at least one electric parameter sensed by the electric state sensor for a characteristic frequency of the rotating electric activity in the cardiac tissue. The pulse generator of the apparatus may then be configured to generate the rotating electric activity synchronization pulses of intervals which are smaller than the reciprocal value of this characteristic frequency. Further, the electric state analyzer may be configured to analyze the at least one electric parameter sensed by the electric state sensor for a dominant frequency as the characteristic frequency of the rotating electric activity in the cardiac tissue.

Preferably, the pulse generator is configured to generate the rotating electric activity synchronization pulses at intervals in a range from 0.6 times the reciprocal value of the characteristic frequency to 0.9 times the reciprocal value of the characteristic frequency.

The pulse applicator of the apparatus for terminating or unpinning rotating electric activity in a cardiac tissue may be configured to generate the rotating electric activity synchronization pulses as unipolar electric pulses of a same polarity, and to generate the rotating electric activity termination or unpinning pulse as a bipolar electric pulse. The rotating electric activity termination or unpinning pulse being a bipolar electric pulse avoids electrically charging the cardiac tissue to a relevant extent. Nevertheless, the electric energy applied during a first part of the rotating electric activity termination or unpinning pulse may include more than 60 or 70% of the electric energy applied by the entire rotating electric activity termination or unpinning pulse. The rotating electric activity synchronization pulses may also be bipolar. But this will normally not provide any additional benefit. The first part of the rotating electric activity termination or unpinning pulse may have the same or the opposite polarity as compared to the rotating electric activity synchronization pulses. However, the relative polarity of the rotating electric activity termination or unpinning pulse will have an influence on the optimum second interval at which the rotating electric activity termination or unpinning pulse is applied after the last rotating electric activity synchronization pulse.

The electric pulses generated by the pulse generator of the apparatus for terminating or unpinning rotating electric activity in a cardiac tissue may additionally include a plurality of anti-tachycardia pacing (ATP) pulses at intervals smaller than the reciprocal value of the characteristic frequency and succeeding the rotating electric activity termination or unpinning pulse. Such anti-tachycardia pacing pulses may be locally applied by a known bipolar electrode of standard ATP configuration, and they will be of a typical ATP electric pulse energy, i.e. of a much smaller electric pulse energy than both the second electric pulse energy of the rotating electric activity termination or unpinning pulse and the first electric pulse energy of the rotating electric activity synchronization pulses.

The pulse generator of the apparatus for terminating or unpinning rotating electric activity in a cardiac tissue may further be configured to generate further electric pulses in response to the electric state analyzer analyzing that there is still rotating electric activity in the cardiac tissue after the application of the electric pulses. I.e. the apparatus may try more than once to terminate or unpin the rotating electric activity by means of a plurality of electric activity synchronization pulses and a succeeding electric rotating activity termination or unpinning pulse.

The pulse applicator of the apparatus for terminating or unpinning rotating electric activity in a cardiac tissue may be configured to apply all rotating electric activity synchronization and rotating electric activity termination or unpinning pulses as electric field pulses extending between a same electrode and a same counter electrode. This means that all electric pulses may have a same direction of the electrical field caused.

Now referring in greater detail to the drawings, the apparatus 1 for terminating or unpinning rotating electric activity in a cardiac tissue depicted in FIG. 1 is configured to terminate or unpin rotating electric activity 2 in a cardiac tissue 3. The rotating electric activity 2 is schematically indicated here by a circular arrow 4 rotating about an inhomogeneity 5 of the cardiac tissue 3. A pair of electrodes 6, 7 provides an electric state sensor 8 which senses at least one electric parameter of the cardiac tissue, like for example a voltage between the electrodes 6 and 7. If the cardiac tissue 3 is a living heart, one of the electrodes, like for example the electrode 6, will typically be placed within the heart, whereas the other electrode, like for example the electrode 7, may be placed outside the heart and even outside a thorax surrounding the heart. The electric parameter sensed by the electric state sensor 8 including the electrodes 6 and 7 is analyzed by an electric state analyzer 9. The electric state analyzer 9 is located within a housing 10. The electrodes 6 and 7 are connected to the analyzer via external lines 11 and 12, connectors 13 and 14 provided at the housing 10 and internal lines 15 and 16. The electric state analyzer 9 analyzes the at least one electric parameter sensed by the electric state sensor 8 for rotating electric activity 2 in the cardiac tissue 3. If the electric state analyzer 9 analyzes that there is rotating electric activity 2 in the cardiac tissue 3, the analyzer determines a characteristic frequency of the rotating electric activity 2 and forwards control signals 17 and 18 which are indicative on the fact that there is rotating electric activity 2 in the cardiac tissue 3 and its characteristic frequency, respectively, to a pulse generator 19. The generator 19 then generates electric pulses which are applied to the cardiac tissue 3 via the electrodes 6 and 7 now acting as a pulse applicator 20 applying the electric pulses as electric field pulses extending across the cardiac tissue 3. These electric pulses include a plurality of rotating electric activity synchronization pulses followed by a rotating electric activity termination or unpinning pulse of a higher maximum electric field strength and electric pulse energy. The electrodes 6 and 7 are unipolar electrodes, they may be arranged in various geometries, and they may be supplemented by additional unipolar electrodes for applying the rotating electric activity synchronization pulses and the rotating electric activity termination or unpinning pulse as electric field pulses. Further, the pulse applicator 20 may include a bipolar electrode 30 for ATP also connected to the generator 20 and to the cardiac tissue 3.

Figure 2:
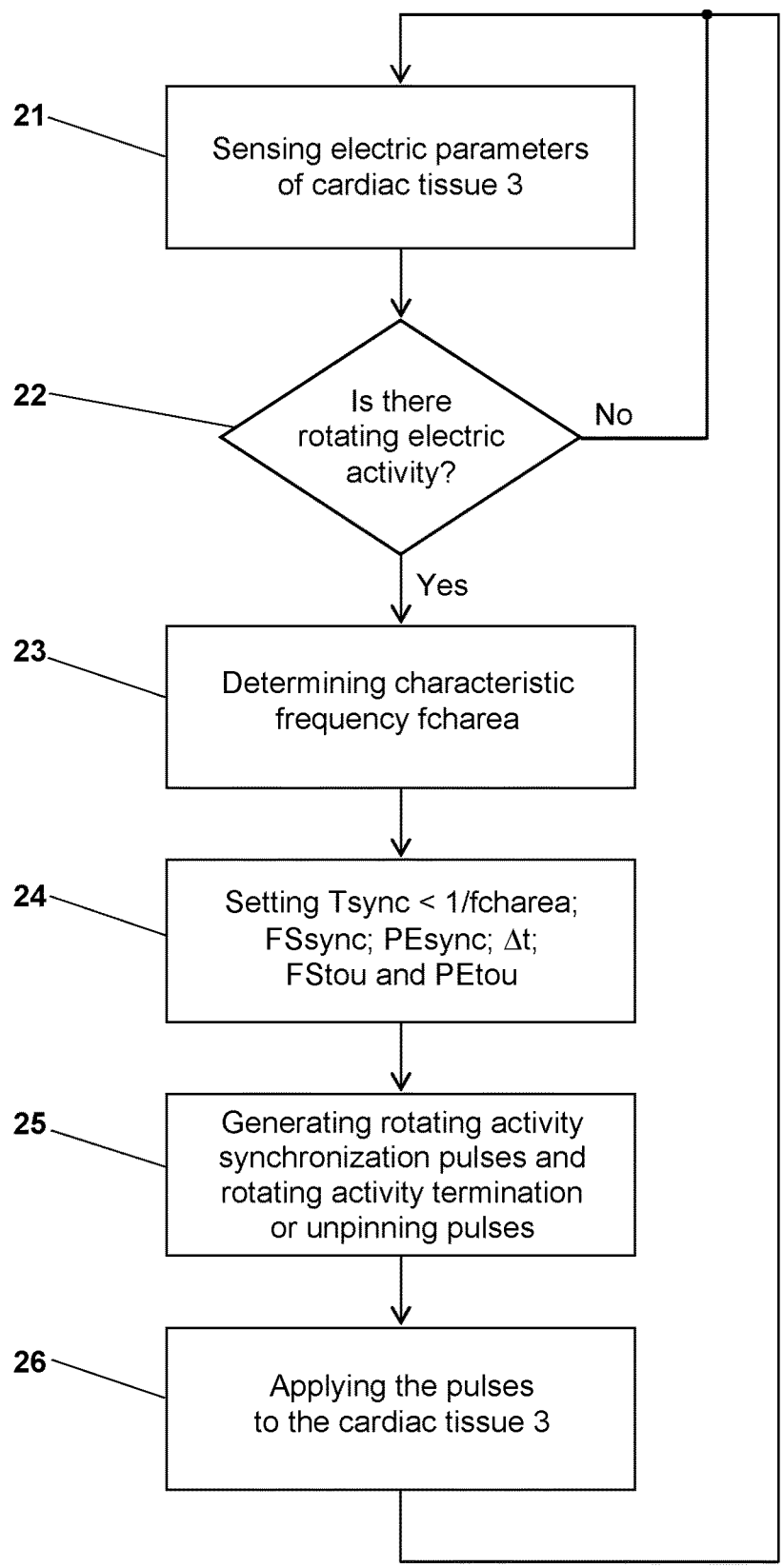
FIG. 2 is a flow chart illustrating the operation of the apparatus for terminating or unpinning rotating electric activity in a cardiac tissue.

The flow chart according to FIG. 2 illustrates the operation of the apparatus 1 according to FIG. 1. The flow chart starts with a step 21 of sensing the at least one electric parameter of the cardiac tissue 3. In a next step 22, the electric parameter is analyzed for the presence of rotating electric activity 2. If there is no rotating electric activity, the operation of the apparatus 1 returns to step 21. If there is rotating electric activity 2, a characteristic frequency fcharea of the rotating electric activity is determined in a step 23. This characteristic frequency fcharea may be the dominant frequency of the rotating electric activity 2.

Next, in a step 24, various parameters of the electric pulses to be generated by the pulse generator 19 are set. These parameters include intervals Tsync, which are set smaller than a reciprocal value of the dominant frequency fcharea, a maximum field strength FSsync to be caused by the rotating electric activity synchronization pulses, and their pulse energy PEsync. Further, an interval Δt between the final rotating electric activity synchronization pulse and the rotating electric activity termination or unpinning pulse, a maximum field strength FStou and an electric pulse energy PEtou of the rotating electric activity termination or unpinning pulse are set. In a step 25, the rotating activity synchronization pulses and the rotating activity termination or unpinning pulse are generated according to the parameters set in step 24. In step 26 these electric pulses are applied to the cardiac tissue 3. Afterwards, the at least one electric parameter of the cardiac tissue 3 is sensed again and analyzed for the presence of rotating electric activity 2, i.e. the operation of the apparatus 1 once again starts with steps 21 and 22.

Figure 3:
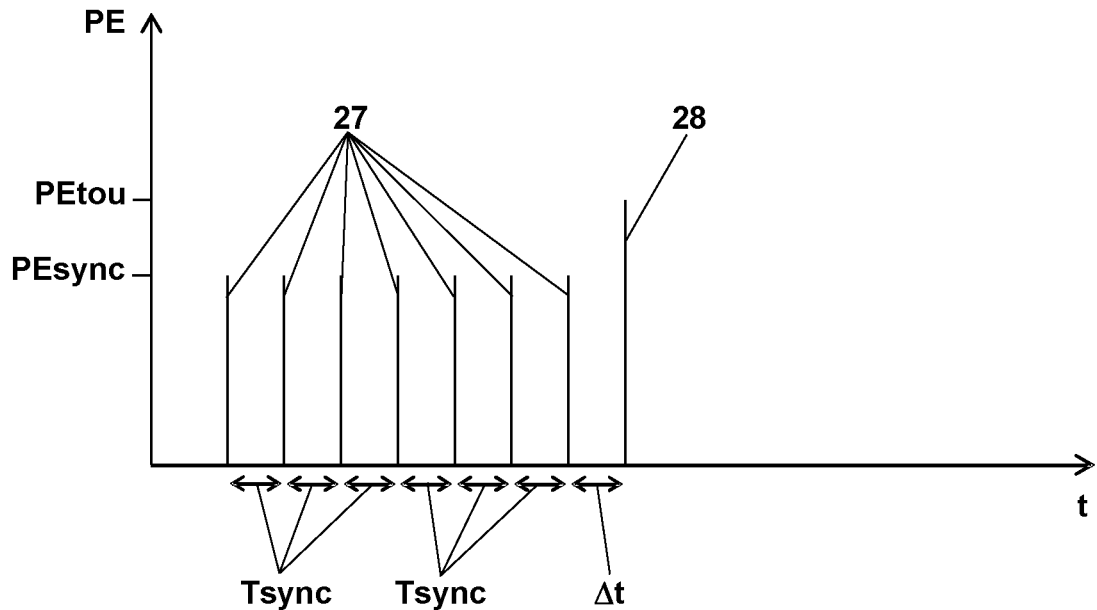
FIG. 3 schematically shows the electric energy applied by electric pulses provided by the apparatus for terminating or unpinning rotating electric activity in a cardiac tissue, and their temporal sequence according to a first embodiment.

FIG. 3 indicates the electric pulse energies PEsync and PEtou depending on the maximum electric field strengths FSsync and FStou of seven electric activity synchronization pulses 27 followed by a single rotating electric activity termination or unpinning pulse 28. FIG. 3 shows that the electric pulse energy PEsync is the same for all electric activity synchronization pulses 27, and that the rotating electric activity synchronization pulses 27 are all arranged at same intervals Tsync in time t. The following rotating electric activity termination or unpinning pulse is arranged at the interval Δt which is typically smaller than the interval Tsync. Generally it is in a range of 0.7 to 1.2 times Tsync. Additionally, the electric pulse energy PEtou of the rotating electric activity termination or unpinning pulse 28 is clearly higher than the electric pulse energy PEsync. The same applies to the respective maximum electric field strengths FSsync and FStou. Both the maximum field strength FStou and the pulse energy of the rotating electric activity termination or unpinning pulse 28 are in ranges typical for rotating electric activity termination or unpinning pulses according to WO 2012/172027 A2. According to the present disclosure, however, a single rotating activity termination or unpinning pulse 28 is sufficient due to the synchronization of the rotating electric activity by means of the rotating electric activity synchronization pulses 27 preceding the rotating electric activity termination or unpinning pulse 28.

Figure 4:
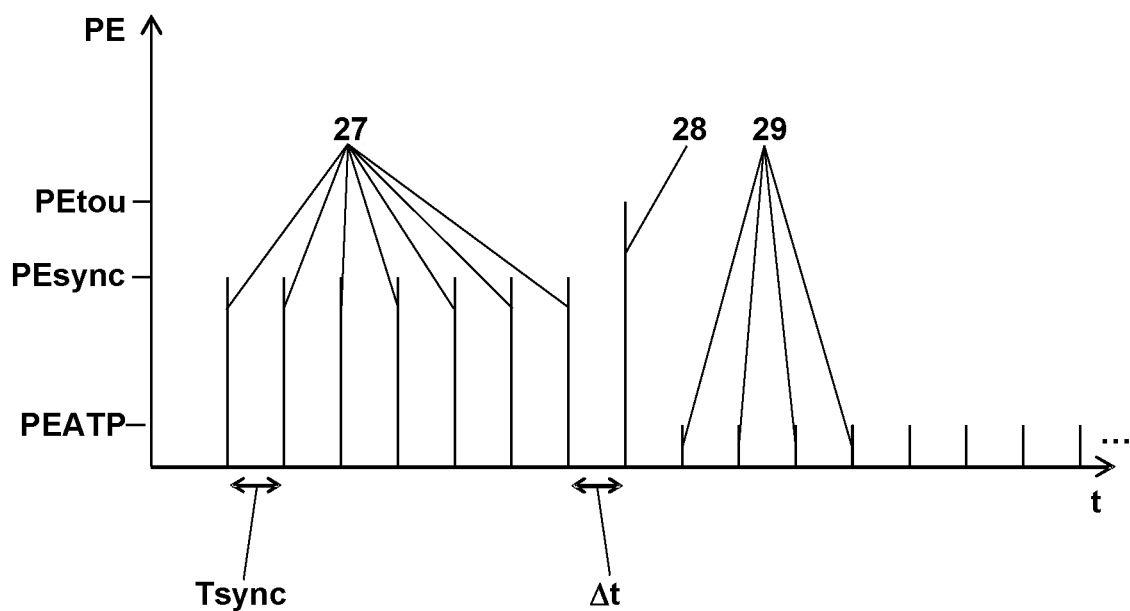
FIG. 4 schematically shows the electric energy applied by electric pulses provided by the apparatus for terminating or unpinning rotating electric activity in a cardiac tissue, and their temporal sequence according to a second embodiment.

FIG. 4, in addition to FIG. 3 also shows a plurality of anti-tachycardia pacing (ATP) pulses 29 succeeding the rotating activity termination or unpinning pulse 28. The anti-tachycardia pacing pulses 29 are applied by the bipolar electrode 30 of FIG. 1. The anti-tachycardia pacing pulses 29 are depicted as being arranged at same intervals in time as the rotating electric activity synchronization pulses 27 but as being of a much smaller electric pulse energy PEATP than the electric pulse energy PEsync of the rotating electric activity synchronization pulses 27. Further, the anti-tachycardia pacing pulses 29 may alternatively be arranged at different intervals in time as compared to the rotating electric activity synchronization pulses 27. The parameters of the anti-tachycardia pacing pulses 29 may be set and the anti-tachycardia pacing pulses 29 may be applied according to the general knowledge of those skilled in the art of anti-tachycardia pacing.

Figure 5:
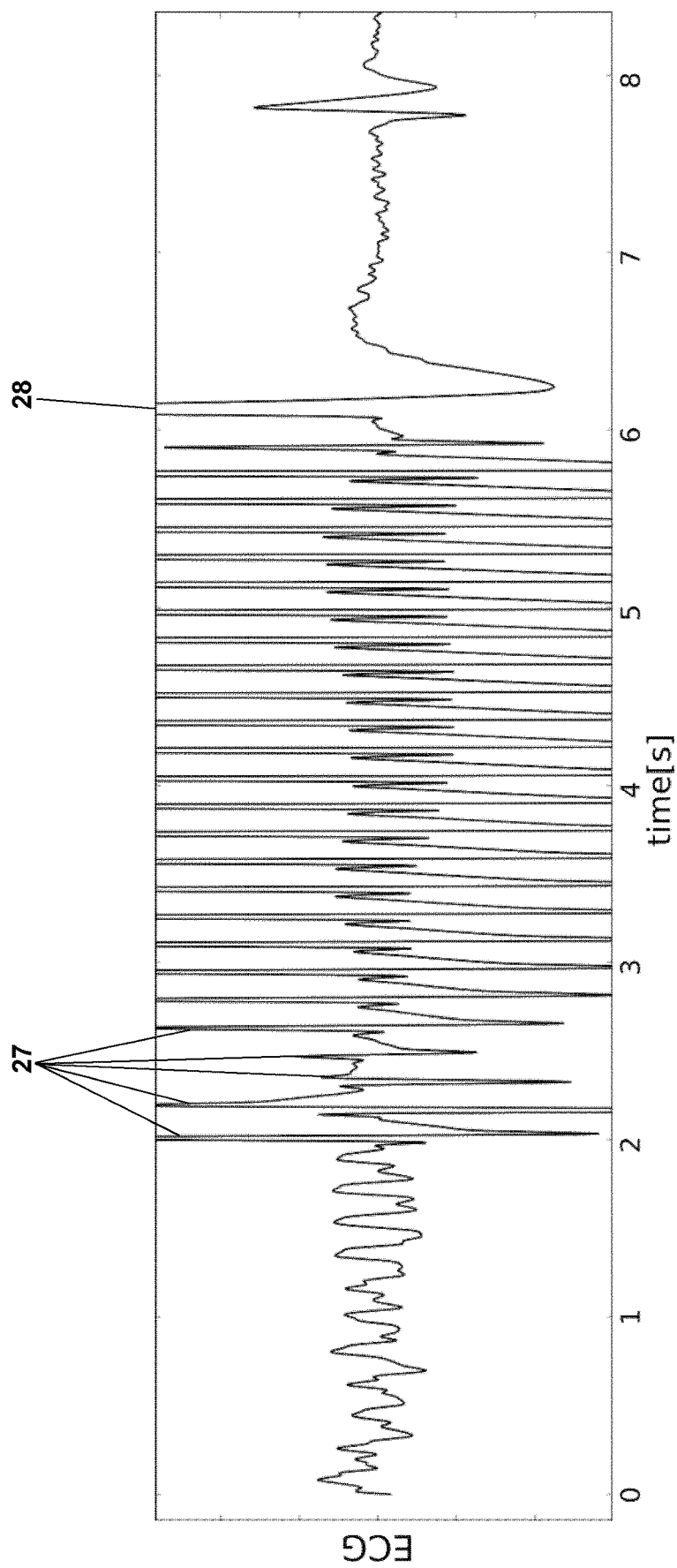
FIG. 5 depicts a time series of an electrocardiogram (ECG) showing successful termination of a ventricular fibrillation in a pig heart.

FIG. 5 depicts a time series of an electrocardiogram (ECG) showing successful termination of ventricular fibrillation in a pig heart in a Langendorff perfusion setup at t=6.1 s. This termination was achieved by applying 25 rotating electric activity synchronization pulses 27 starting at t=2 s, and one rotating electric activity termination or unpinning pulse 28. The rotating electric activity termination or unpinning pulse 28 had a field strength of a comparable magnitude to that required in the same setup to terminate ventricular fibrillation according to WO 2012/172027 A2. The electric field strength of the rotating electric activity synchronization pulses was less than 11% of the electric field strength of the rotating electric activity termination or unpinning pulse 28.

Figure 6:
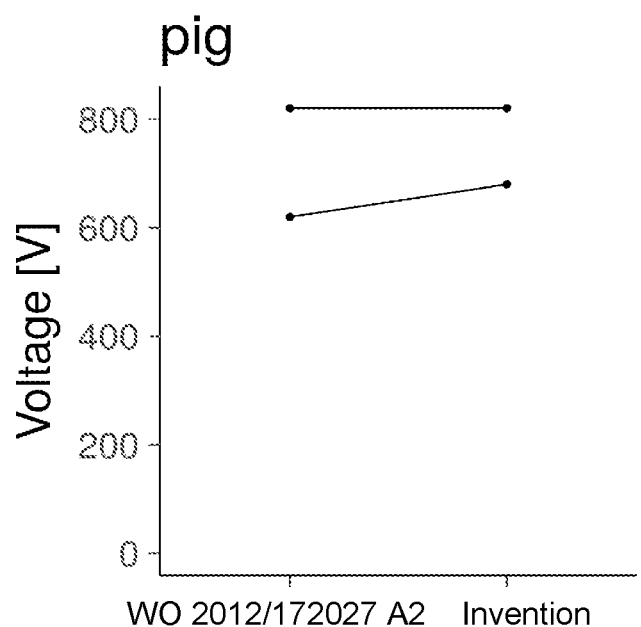
FIG. 6 depicts data of experiments with pig hearts and compares the voltage of rotating electric activity termination or unpinning pulses applied after rotating electric activity synchronization pulses with the voltage of each of a plurality of rotating electric activity termination or unpinning pulses applied according to WO 2012/172027 A2.

FIG. 6 depicts data of whole-heart Langendorff perfusion experiments with pig hearts and compares the voltage of the rotating electric activity termination or unpinning pulse 28 applied by the apparatus for terminating or unpinning rotating electric activity in a cardiac tissue with the voltage of rotating electric activity termination or unpinning pulses according to WO 2012/172027 A2, that are required for a probability of 0.5 to terminate ventricular fibrillation. Two dots connected by a line correspond to one experiment. The required voltages differ among the experiments, but within one experiment they are similar. As the rotating electric activity synchronization pulses are of much lower voltage, the total energy applied by the apparatus according to the present disclosure for terminating the ventricular fibrillation is significantly lower than the total energy applied by the apparatus according to WO 2012/172027 A2.

Figure 7:
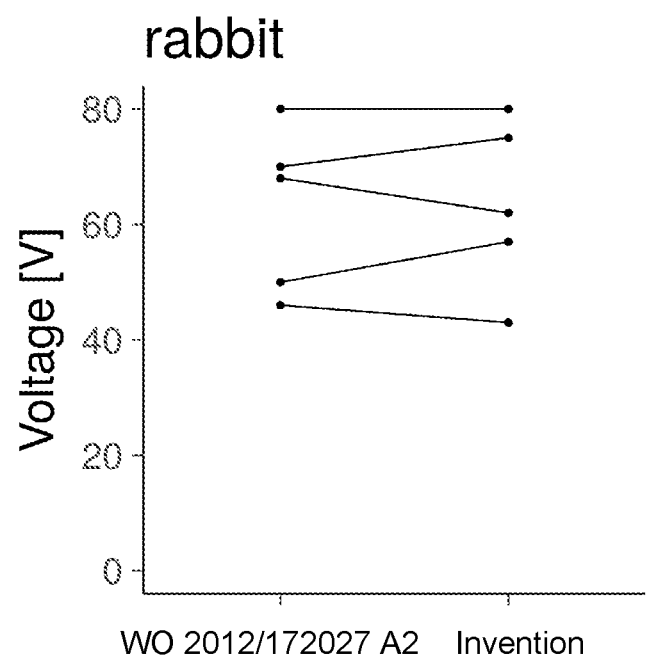
FIG. 7 depicts data of experiments with rabbit hearts which otherwise correspond to the experiments according to FIG. 6.

FIG. 7 depicts data of whole heart Langendorff perfusion experiments with rabbit hearts and compares the voltage of the rotating electric activity termination or unpinning pulse applied by the apparatus for terminating or unpinning rotating electric activity in a cardiac tissue with the voltage of rotating electric activity termination or unpinning pulses applied according to WO 2012/172027 A2, that are required for a probability of 0.5 to terminate ventricular fibrillation. Two dots connected by a line correspond to one experiment. The required voltages differ among the experiments, but within one experiment they are similar. As the rotating electric activity synchronization pulses are of a much lower voltage, the total energy applied by the apparatus according to the present disclosure is significantly lower than the total energy applied by the apparatus according to WO 2012/172027 A2.

Many variations and modifications may be made to the preferred embodiments of the invention without departing substantially from the spirit and principles of the invention. All such modifications and variations are intended to be included herein within the scope of the present invention, as defined by the following claims.

We claim:

1. An apparatus for terminating or unpinning a rotating electric activity in a cardiac tissue, the apparatus comprising:
   an electric state sensor configured to sense at least one electric parameter of the cardiac tissue;
   an electric state analyzer connected to the electric state sensor and configured to analyze the at least one electric parameter sensed by the electric state sensor for the rotating electric activity in the cardiac tissue;
   a pulse generator connected to the electric state analyzer and configured to generate electric pulses in response to the electric state analyzer analyzing that there is the rotating electric activity in the cardiac tissue, the electric pulses including a rotating electric activity termination or unpinning pulse; and
   a pulse applicator connected to the pulse generator and configured to apply the electric pulses as electric field pulses extending across the cardiac tissue;
   wherein the electric pulses include a plurality of rotating electric activity synchronization pulses preceding the rotating electric activity termination or unpinning pulse,
   wherein the rotating electric activity synchronization pulses are arranged at first intervals, and the rotating electric activity termination or unpinning pulse is arranged at a second interval in a range from 0.7 to 1.2 times one of the first intervals after the last one of the plurality of rotating electric activity synchronization pulses, and wherein at least one of
a first maximum electric field strength as caused by each of the rotating electric activity synchronization pulses is not more than 82% of a second maximum electric field strength as caused by the rotating electric activity termination or unpinning pulse; and
a first electric pulse energy delivered to the cardiac tissue by each of the rotating electric activity synchronization pulses is not more than 67% of a second electric pulse energy delivered to the cardiac tissue by the rotating electric activity termination or unpinning pulse.

2. The apparatus of claim 1, wherein a number of the rotating electric activity synchronization pulses preceding the rotating electric activity termination or unpinning pulse is at least five.

3. The apparatus of claim 2, wherein the number of the rotating electric activity synchronization pulses preceding the rotating electric activity termination or unpinning pulse is in a range from 10 to 30.

4. The apparatus of claim 1, wherein the first maximum electric field strength as caused by each of the rotating electric activity synchronization pulses is not more than 71% of the second maximum electric field strength as caused by the rotating electric activity termination or unpinning pulse.

5. The apparatus of claim 4, wherein the first maximum electric field strength as caused by each of the rotating electric activity synchronization pulses is not more than 50% of the second maximum electric field strength as caused by the rotating electric activity termination or unpinning pulse.

6. The apparatus of claim 1, wherein the first maximum electric field strength as caused by each of the rotating electric activity synchronization pulses is in a range from 20 to 200 V/m.

7. The apparatus of claim 1, wherein the first maximum electric field strength as caused by each of the rotating electric activity synchronization pulses is constant.

8. The apparatus of claim 1, wherein the first electric pulse energy delivered to the cardiac tissue by each of the rotating electric activity synchronization pulses is not more than 50% of the second electric pulse energy delivered to the cardiac tissue by the rotating electric activity termination or unpinning pulse.

9. The apparatus of claim 8, wherein the first electric pulse energy delivered to the cardiac tissue by each of the rotating electric activity synchronization pulses is not more than 25% of the second electric pulse energy delivered to the cardiac tissue by the rotating electric activity termination or unpinning pulse.

10. The apparatus of claim 1, wherein first the electric pulse energy delivered to the cardiac tissue by each of the rotating electric activity synchronization pulses is constant.

11. The apparatus of claim 1, wherein the electric state analyzer is configured to analyze the at least one electric parameter sensed by the electric state sensor for a characteristic frequency of the rotating electric activity in the cardiac tissue, and that the pulse generator is configured to generate the rotating electric activity synchronization pulses at intervals that are shorter than a reciprocal value of the characteristic frequency of the rotating electric activity in the cardiac tissue.

12. The apparatus of claim 11, wherein the electric state analyzer is configured to analyze the at least one electric parameter sensed by the electric state sensor for a dominant frequency as the characteristic frequency of the rotating electric activity in the cardiac tissue.

13. The apparatus of claim 11, wherein the pulse generator is configured to generate the rotating electric activity synchronization pulses at intervals longer than 0.6 times and shorter than 0.9 times the reciprocal value of the characteristic frequency of the rotating electric activity in the cardiac tissue.

14. The apparatus of claim 11, wherein the electric pulses include a plurality of anti-tachycardia pacing pulses at intervals that are shorter than the reciprocal value of the characteristic frequency of the rotating electric activity in the cardiac tissue, the anti-tachycardia pacing pulses succeeding the rotating electric activity termination or unpinning pulse.

15. The apparatus of claim 14, wherein the pulse applicator comprises a separate bipolar electrode connected to the pulse generator and configured to apply the anti-tachycardia pacing pulses to the cardiac tissue.

16. The apparatus of claim 1, wherein the pulse generator is configured to generate further electric pulses in response to the electric state analyzer analyzing that there is still rotating electric activity in the cardiac tissue after the application of the electric pulses.

17. The apparatus of claim 1, wherein the pulse applicator is configured to apply the rotating electric activity synchronization pulses and the rotating electric activity termination or unpinning pulse as electric field pulses extending between a same electrode and a same counter electrode.

18. An apparatus for terminating or unpinning a rotating electric activity in a cardiac tissue, the apparatus comprising:
an electric state sensor configured to sense at least one electric parameter of the cardiac tissue;
an electric state analyzer connected to the electric state sensor and configured to analyze the at least one electric parameter sensed by the electric state sensor for the rotating electric activity in the cardiac tissue;
a pulse generator connected to the electric state analyzer and configured to generate electric pulses in response to the electric state analyzer analyzing that there is the rotating electric activity in the cardiac tissue, the electric pulses including a rotating electric activity termination or unpinning pulse; and
a pulse applicator connected to the pulse generator and configured to apply the electric pulses as electric field pulses extending across the cardiac tissue;
wherein the electric pulses include a plurality of rotating electric activity synchronization pulses preceding the rotating electric activity termination or unpinning pulse,
wherein the rotating electric activity synchronization pulses are arranged at first intervals, and the rotating electric activity termination or unpinning pulse is arranged at a second interval in a range from 0.7 to 1.2 times one of the first intervals after the last one of the plurality of rotating electric activity synchronization pulses,
wherein a first maximum electric field strength as caused by each of the rotating electric activity synchronization pulses is not more than 71% of a second maximum electric field strength as caused by the rotating electric activity termination or unpinning pulse,
wherein a first electric pulse energy delivered to the cardiac tissue by each of the rotating electric activity synchronization pulses is not more than 50% of a second electric pulse energy delivered to the cardiac tissue by the rotating electric activity termination or unpinning pulse, wherein a number of the rotating electric activity synchronization pulses preceding the rotating electric activity termination or unpinning pulse is in a range from 10 to 30, wherein the first maximum electric field strength as caused by each of the rotating electric activity synchronization pulses is in a range from 20 to 200 V/m, wherein the electric state analyzer is configured to analyze the at least one electric parameter sensed by the electric state sensor for a characteristic frequency of the rotating electric activity in the cardiac tissue, and that the pulse generator is configured to generate the rotating electric activity synchronization pulses at intervals at intervals longer than 0.6 times and shorter than 0.9 times a reciprocal value of the characteristic frequency of the rotating electric activity in the cardiac tissue, and wherein the pulse applicator is configured to apply the rotating electric activity synchronization pulses and the rotating electric activity termination or unpinning pulse as electric field pulses extending between a same electrode and a same counter electrode.

19. The apparatus of claim 18, wherein the electric state analyzer is configured to analyze the at least one electric parameter sensed by the electric state sensor for a dominant frequency as the characteristic frequency of the rotating electric activity in the cardiac tissue.

20. The apparatus of claim 18, wherein the electric pulses include a plurality of anti-tachycardia pacing pulses at intervals that are shorter than the reciprocal value of the characteristic frequency of the rotating electric activity in the cardiac tissue, the anti-tachycardia pacing pulses succeeding the rotating electric activity termination or unpinning pulse, and wherein the pulse applicator comprises a separate bipolar electrode connected to the pulse generator and configured to apply the anti-tachycardia pacing pulses to the cardiac tissue.

* * * * *